United States Patent [19]

Henry et al.

[11] Patent Number: 4,480,482

[45] Date of Patent: Nov. 6, 1984

[54] ELASTIC LIMIT DETECTION AND RESET TESTING SYSTEM

[76] Inventors: Robert R. Henry, 307 Lakeside Dr., Lafayette, La. 70508; William C. Heldenbrand, P.O. Box 2066, New Iberia, La. 70560

[21] Appl. No.: 454,323

[22] Filed: Dec. 29, 1982

[51] Int. Cl.³ .............................................. G01N 3/10
[52] U.S. Cl. ........................................ 73/805; 73/789
[58] Field of Search ................. 73/805, 769, 789, 807, 73/826

[56] References Cited

U.S. PATENT DOCUMENTS 3,554,019  1/1971  Van Den Hove et al. ...... 73/826 X

OTHER PUBLICATIONS

H. T. Strandrud, "Structural Fatigue Testing by Computer Control", ISA Aerospace Instrumentation Symposium, May 5-7, 1969, Las Vegas, Nevada; p. 253.

Primary Examiner—Jerry W. Myracle
Attorney, Agent, or Firm—Harvey B. Jacobson

[57] ABSTRACT

The signal output of a pressure transducer, measuring the increasing tensile load above a minimum level on a test specimen, is differentiated to produce an analog slope signal compared with an adjusted sensitivity voltage to generate a reset signal when the elastic limit of the specimen is exceeded. Through digital gate logic enabled above a minimum tensile load, the reset signal terminates loading of the specimen to prevent destruction thereof.

5 Claims, 4 Drawing Figures

ELASTIC LIMIT DETECTION AND RESET TESTING SYSTEM

BACKGROUND OF THE INVENTION

This invention relates generally to the testing of materials or products for tensile strength.

Tensile strength testing of a product or specimen is generally well known. In one form of testing apparatus, the specimen is anchored to a frame and placed under an increasing tensile load by a fluid power mechanism in order to measure and display its tensile strength on some readout display device. The testing apparatus is adjusted to handle a given class of products that fall within an expected range of elastic tensile strength and the load applied during each test operation does not exceed an expected elastic limit. Accordingly, relatively weak products when tested are stressed beyond their elastic limit and sometimes into the plastic region of their tensile stress characteristic causing either permanent set or rupture.

It is therefore an important object of the present invention to prevent unintentional destructive testing of products normal subjected to normal tensile loading in a tension testing operation.

SUMMARY OF THE INVENTION

In accordance with the present invention, a fluid power operated testing apparatus is automatically reset when the tensile stress induced exceeds the elastic limit, whatever value it may be, for the specimen undergoing the test. In this fashion, destruction of the test specimen is avoided. Automatic reset is therefore operative to terminate the testing operation by deenergizing the powered testing apparatus through which an increasing tensile load is applied to the test specimen during the test operation. Toward that end, the tensile load signal being measured and displayed by the testing apparatus is differentiated to produce an analog slope signal reflecting the rate of change in the tensile load or stress on the test specimen. When the slope signal decreased below an adjusted level, a reset signal is generated to terminate the testing operation by removal of the tensile load on the specimen.

The reset signal is transmitted through digital gate logic enabled when the tensile load signal exceeds a minimum level in order to prevent premature or unintended reset of the testing apparatus. Toward that end, an adjustable threshold level detector is connected to the output of the pressure signal transducer through which the tensile load on the specimen is continuously measured for display purposes and through which an analog input is supplied to a signal differentiator generating the analog slope signal aforementioned.

BRIEF DESCRIPTION OF DRAWING FIGURES

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF PREFERRED EMBODIMENT

Figure 1:
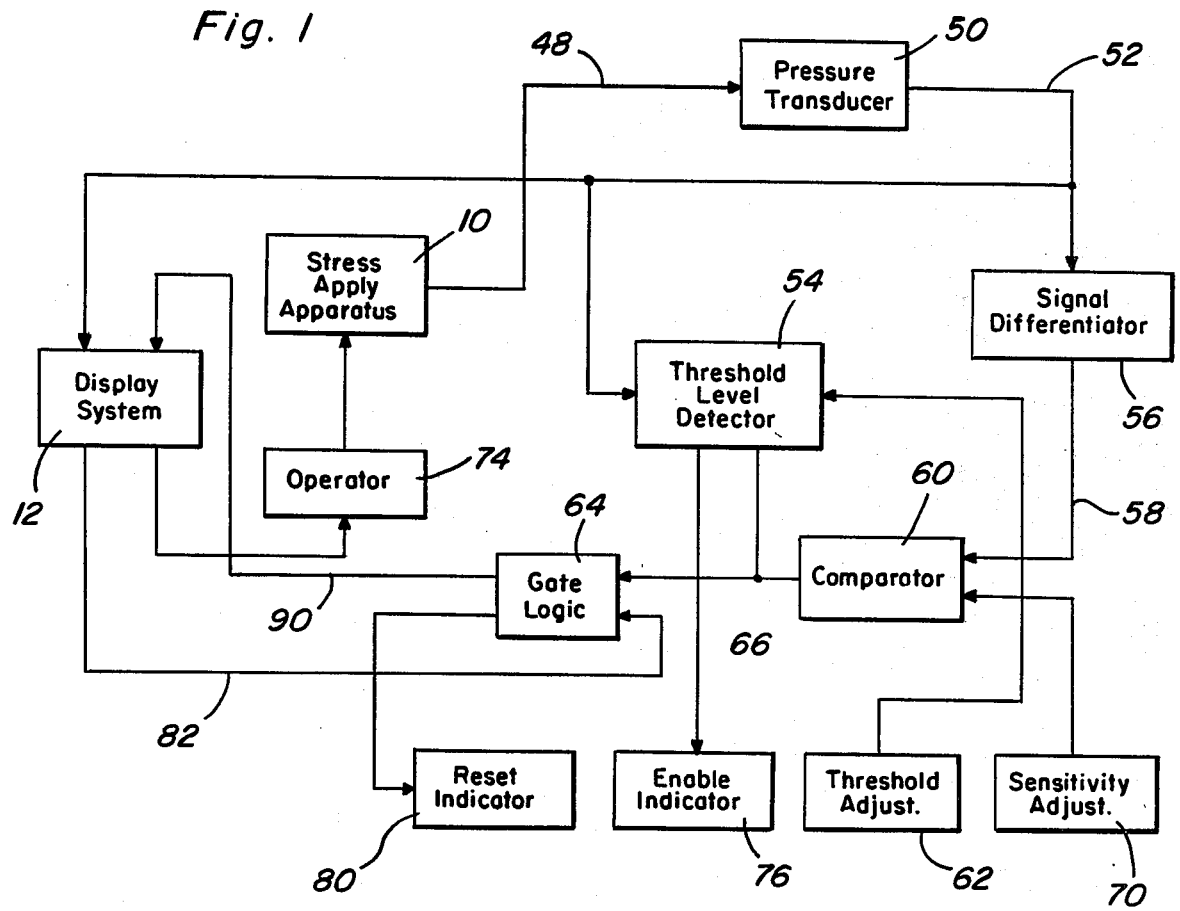
FIG. 1 is a block diagram illustrating the system of the present invention.
Figure 2:
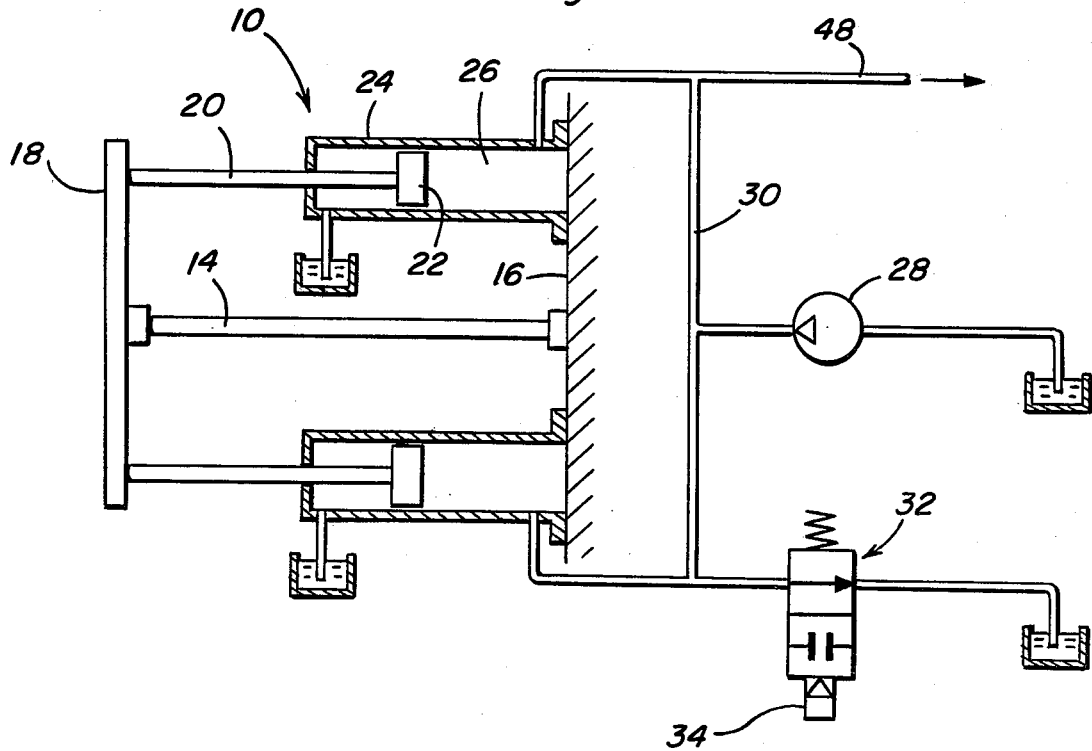
FIG. 2 is a simplified fluid circuit diagram illustrating the testing apparatus with which the invention is associated.

Referring now to the drawings in detail, FIG. 1 diagrammatically illustrates a system for controlling operation of an apparatus 10 by means of which a test specimen is stressed and the loading placed thereon during testing monitored through a display system 12. Such stress applying apparatus and display systems are generally well known. FIG. 2 shows for example, one type of apparatus 10 utilized for applying tensile loads to an elastic test specimen 14 anchored at opposite longitudinal ends to a stationary frame 16 and a movable bar 18 to which a pair of piston rods 20 are connected. The rods 20 extend from pistons 22 through fluid pressure cylinders 24 anchored to the frame. The cylinders enclose pressure chambers 26 to which pressurized fluid is supplied by a powered pump 28 through a pump pressure line 30. The pump pressure line is maintained depressurized by a control valve 32 biased to an open position as shown. Upon displacement of the valve to a closed position by energization of its actuator 34, the chambers 26 are pressurized to apply an increasing force or load on the specimen 14 causing tensile elongation or strain thereof and expansion of the pressure chambers 26. At the end of the test, the chambers 26 are depressurized and contract as the specimen returns to its undeformed state, assuming the test is limited to strain of the specimen below its elastic limit.

Figure 4:
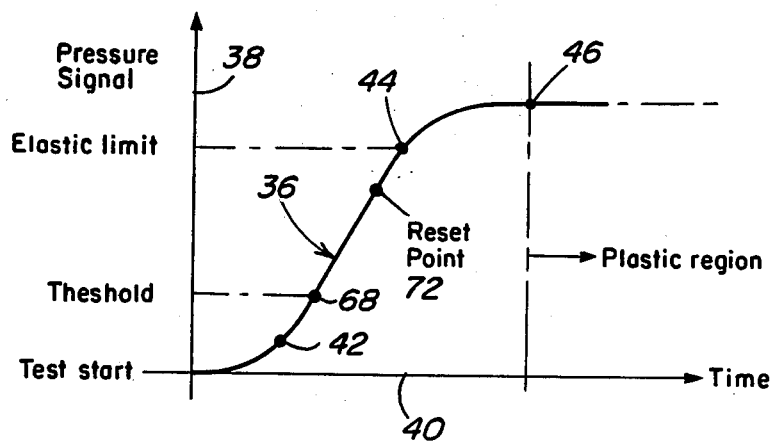
FIG. 4 is a graphical illustration of test specimen characteristics.

FIG. 4 graphically illustrates the characteristics of a typical elastic specimen subjected to the foregoing testing. The curve 36 represents the increasing load applied to the specimen as reflected by the pressure signal in pressure line 30 measured along ordinate 38 as a function of time denoted along abscissa 40. At the beginning of the test, the load increases non-linearly to a point 42, and then continues to increase as a substantially linear function of time to a point 44 representing the elastic limit of the specimen. Between points 42 and 44, the load increases as indicated by the slope of curve 36 with minimum deviation from a fixed rate of change. At point 44, the load increases non-linearly until point 46 corresponding to the plastic region of the specimen characteristic from which point the specimen continues to be deformed without any increase in load until rupture or failure occurs. It is accordingly desireable to terminate testing before point 46 is reached and preferably below the elastic limit point 44 to avoid permanent set of the specimen.

As shown in FIG. 1, the pressure line from apparatus 10 is connected by a pressure signal line 48 to a transducer device 50 of any well known type for generating an electic analog signal proportional in magnitude to the pressure in the chambers 26 or load applied to the specimen 14. The analog pressure signal is applied through line 52 to the display 12, to a signal threshold level detector 54 and to a signal differentiator 56 from which an analog slope signal is fed by line 58 to a comparator 60. The threshold level detector 54 is connected to a level adjusting device 62 to set the signal level above which the detector enables a gate logic section 64 through line 66. In this manner, an adjusted threshold point 68 as depicted in FIG. 4 is established for certain specimens. A sensitivity level adjusting device 70 on the other hand is connected to the comparator 60 for producing a reset output therefrom, applied to line 66, when the slope signal decreases below an adjusted value corresponding to the slope of curve 36 at a reset point 72 as depicted in FIG. 4. When such reset signal is produced by comparator 60 in line 66, the previously enabled gate logic 64 transmits the reset signal to the display system for terminating the testing operation through operator 74. An indicator 76 connected to detector 54 indicates enabling of the gate logic 64 above a minimum load level at point 68 on curve 36 after a testing operation is initiated. Generation of the reset signal is registered by indicator 80 connected to the gate logic.

Figure 3:
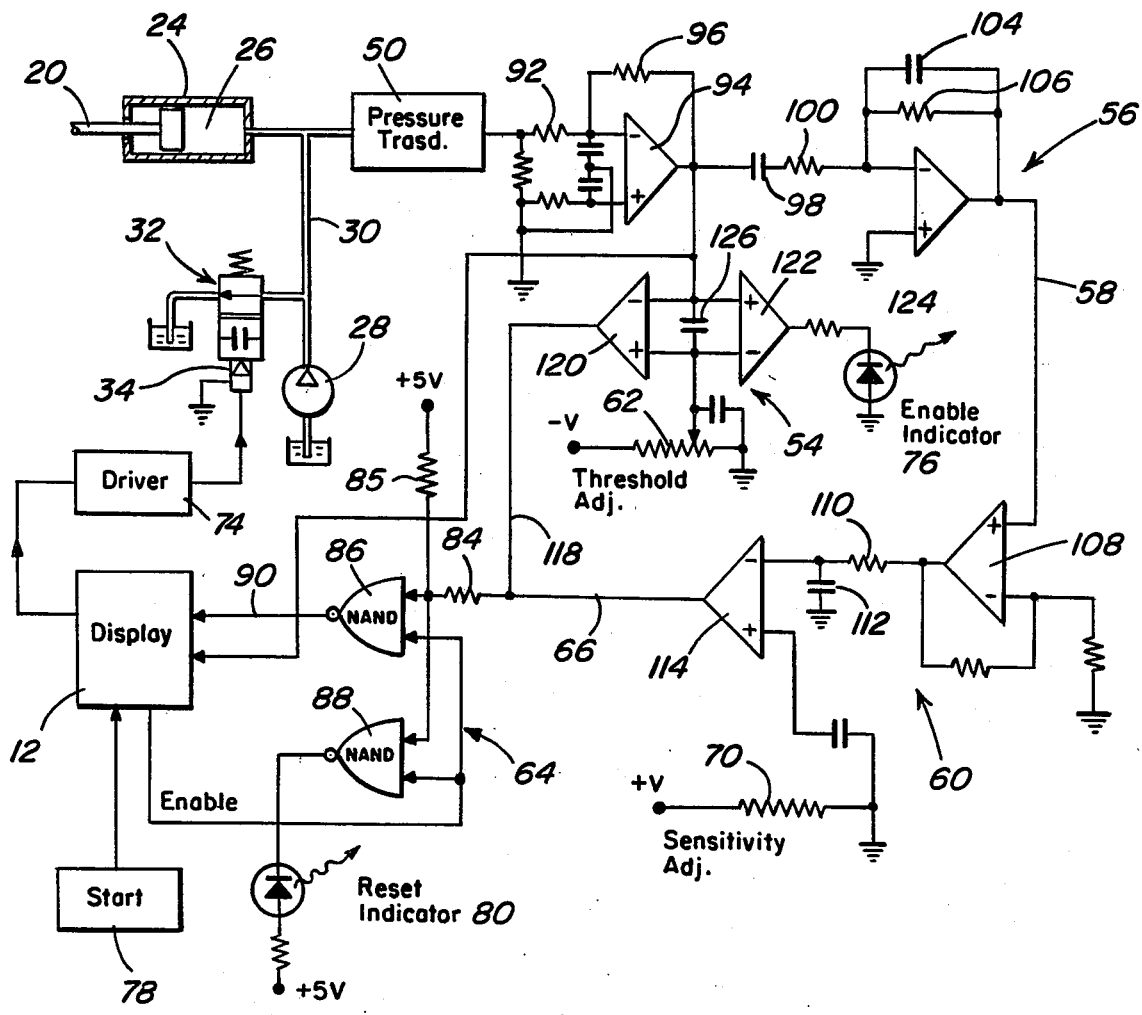
FIG. 3 is an electrical circuit diagram illustrating in greater detail the system depicted in FIG. 1.

Referring now to the circuit of FIG. 3, operation of the invention will become apparent. In the quiescent condition of the circuit as shown, the valve 32 is in an open position with its actuator 34 deenergized so that the pressure chambers 26 of the tension applying apparatus are depressurized. An enable line 82 is in a low logic state while comparator 120 through resistor 84 maintains a low logic state on the gate logic section so that lows are applied to one of the inputs of each of the NAND gates 86 and 88 producing highs at their outputs. Accordingly, in the quiescent state the pressure signal 52 is below the threshold level corresponding to 68 in FIG. 4 which produces a high in reset line 90 disabling the reset system and the high at the output of NAND gate 88 holds the LED indicator 80 disabled.

At the beginning of a testing operation initiated by actuation of a start control 78, the display system 12 applies a high logic voltage to enable input line 82 and an operating voltage to driver 74 to cause actuation of the valve 32 to its closed position. The output of pump 28 will then apply fluid under increasing pressure to the pressure chambers 26 of the tension applying apparatus. The tensile specimen 14 will then be subject to an increasing tensile stress proportional to the analog pressure signal generated by transducer 50 connected to the pump output line 30. The pressure signal output of transducer 50 is applied through resistor 92 to the inverting input of signal amplifier 94 arranged in a configuration including feedback resistor 96 to provide an amplified output proportional to the analog pressure signal input. The amplified pressure signal is differentiated and filtered in the signal differentiator 56 by operational amplifier 102 arranged in a signal differentiating configuration by parallel connected, feedback capacitor 104 and resistor 106 and series connected capacitor 98 and resistor 100. The output of amplifier 102 will accordingly provide a slope signal in line 58 proportional to the rate of change of the input pressure signal or tensile stress on the specimen undergoing the testing operation. The slope signal is applied to the non-inverting input of an amplifier 108 and is amplified and filtered by resistor 110 and grounded capacitor 112 to supply a processed slope signal to the inverting output of a comparator amplifier 114 with an open-collector output corresponding to comparator 60. The other non-inverting input of comparator 114 receives a fixed reference voltage of adjusted level determined by the setting of sensitivity control 70. Accordingly, when the amplified and filtered slope signal or rate of change in tensile stress on the specimen decreases below the reset level corresponding to point 72 on the curve 36 of FIG. 4, an output is produced by the comparator in line 66 coupled by resistor 84 and pull-up resistor 85 to inputs of the NAND gates 86 and 88 in the gate logic section 64.

Until such output of comparator 60 is generated, line 66 is maintained in a low voltage state as aforementioned so that the high logic voltage in enable line 82 applied to the other inputs of the NAND gates 86 and 88 will maintain high level outputs in reset line 90 from NAND gate 86 and in the indicator line 116 to the reset indicator 80. When the high from comparator 60 is applied to NAND gates 86 and 88, a low is produced at the outputs thereof to effect reset through driver 74 and enable reset indicator 80 so as to signify reset. With reset, the valve actuator 34 is de-energized to open valve 32 thereby depressurizing the pressure chambers 26 of the tension applying apparatus 10.

The output of comparator 60 triggering reset as aforementioned, is prevented by a negative output in line 118 from one of the outputs of the detector 54 having a pair of open collecter type comparators 120 and 122 with respectively inverting and non-inverting inputs interconnected. The other output of the detector 54 from the comparator 122 is connected by resistor 124 to the enable indicator 76. The inputs of the amplifiers 120 and 122 are coupled by a capacitor 126, with one pair of interconnected inputs connected to the output of the input signal amplifier 94 while the other pair of interconnected inputs is connected to the threshold adjusting resistor 62. The voltage level of the input signal is therefore compared with an adjusted threshold voltage level to unclamp line 118 from amplifier 120 when the input signal level exceeds the adjusted threshold level corresponding to point 68 on the graph of FIG. 4. At the same time, the output of amplifier 122 goes negative to conduct current from ground through LED indicator 76 turning it on to signify the progress of the testing operation.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. In combination with powered stress testing apparatus for applying an increasing tensile load to an elastic specimen, a transducer device connected to the apparatus for continuously measuring the tensile load exerted on the specimen, display means connected to the transducer device for displaying the measured tensile load on the specimen during testing thereof, and signal processing means connected to the transducer device for generating a slope signal substantially proportional to the rate of change of the increasing tensile load, the improvement residing in means for limiting said testing of the specimen to a tensile load range during which the slope signal is substantially constant in magnitude, comprising means connected to the transducer device for detecting measurement of an increase in said tensile load above a lower limit of the tensile load range, comparator means connected to the signal processing means for generating a reset signal in response to deviations of said slope signal from the constant magnitude and logic means enabled by said detecting means above the lower limit of the tensile load range for terminating said testing of the specimen by the apparatus in response to said reset signal.

2. The improvement as defined in claim 1 including indicator means connected to the detecting means and the logic means for sequentially signifying said enabling of the logic means and said generation of the reset signal.

3. In combination with powered stress testing apparatus for applying an increasing tensile load to an elastic specimen, a transducer device for measuring the tensile load applied, and signal processing means connected to the transducer device for generating a slope signal substantially proportional to the rate of change of the increasing tensile load, the improvement residing in reset control means for limiting said testing of the specimen to measurement of the tensile load during which the slope signal is substantially constant in magnitude, comprising means connected to the transconducer device for detecting measurement of an increase in said tensile load above a lower limit, comparator means connected to the signal processing means for generating a reset signal in response to deviations of said slope signal from the constant magnitude, and logic means enabled by said detecting means above the lower limit of the tensile load for terminating said testing of the specimen by the apparatus in response to said reset signal.

4. In combination with a static stress testing apparatus for applying an increasing load to a test specimen having an elastic limit below which the specimen exhibits a substantially linear stress-strain characteristic, transducer means connected to the apparatus for continuously measuring the load applied to the specimen during a test interval, signal differentiating means connected to the transducer means for generating an analog signal substantially proportional to the rate of change of said increasing load, reset means responsive to excessive deviation of said analog signal from a substantially constant level for interrupting operation of the testing apparatus to terminate said test interval and means for disabling the reset means below a minimum value of the load applied to the test specimen.

5. The combination of claim 4 including means for adjusting the detection of said excessive deviation by the reset means to terminate loading of the specimen below the elastic limit thereof.

* * * * *